United States Patent [19]

Tonne et al.

[11] Patent Number: 4,736,040

[45] Date of Patent: Apr. 5, 1988

[54] PREPARATION OF 1,2-BENZISOTHIAZOLONES

[75] Inventors: Peter Tonne, Neustadt; Hagen Jaedicke, Ludwigshafen, both of Fed. Rep. of Germany

[73] Assignee: BASF Aktiengesellschaft, Ludwigshafen, Fed. Rep. of Germany

[21] Appl. No.: 815,918

[22] Filed: Jan. 2, 1986

[30] Foreign Application Priority Data

Jan. 10, 1985 [DE] Fed. Rep. of Germany ....... 3500577

[51] Int. Cl.$^4$ ............................................. C07D 275/04
[52] U.S. Cl. .................................... 548/209; 564/154
[58] Field of Search ................................ 548/207, 209

[56] References Cited

U.S. PATENT DOCUMENTS

| | | | |
|---|---|---|---|
| 2,767,174 | 10/1956 | Katz et al. | 548/209 X |
| 3,012,039 | 12/1961 | Morley | 548/209 |
| 3,759,936 | 9/1973 | Mounier | 548/210 X |
| 4,031,227 | 6/1977 | Jackson | 548/207 X |
| 4,156,729 | 5/1979 | Böshagen et al. | 548/209 X |

FOREIGN PATENT DOCUMENTS

| | | |
|---|---|---|
| 1135468 | 3/1963 | Fed. Rep. of Germany . |
| 1147947 | 1/1964 | Fed. Rep. of Germany . |
| 2652201 | 6/1977 | Fed. Rep. of Germany . |
| 2656227 | 6/1978 | Fed. Rep. of Germany . |

OTHER PUBLICATIONS

A. Reissert and E. Manns, Chem. Ber. 61, (1928), 1308–1309.
H. Hettler, Adv. Het. Chem. 15 (1973), 241.
Il Farmaco, Ed. Scientifica, vol. 23, Nr. 11, Nov. 1975, pp. 1075–1080.

*Primary Examiner*—Donald G. Daus
*Assistant Examiner*—Diana G. Rivers
*Attorney, Agent, or Firm*—John H. Shurtleff

[57] ABSTRACT

1,2-Benzisothiazolones and their alkali metal salts are prepared by reacting 2,2'-dithiodibenzamides in the presence of oxygen or oxygen donors in an aqueous alkaline medium to which a water-soluble organic solvent may be added and, if desired, freeing the benzisothiazolones from the alkali metal salts with acid.

14 Claims, No Drawings

PREPARATION OF 1,2-BENZISOTHIAZOLONES

The present invention relates to the preparation of 1,2-benzisothiazolones and their alkali metal salts by reacting 2,2'-dithiodibenzamides in an aqueous alkaline medium to which a water-soluble organic solvent may be added and, if desired, acidifying the reaction mixture.

1,2-Benzisothiazolones of the general formula (II) can, as is known, be prepared by disproportionation of amides of 2,2'-dithiodibenzoic acids (I) in an aqueous alkaline medium in accordance with the following equation:

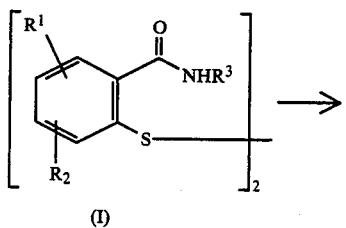

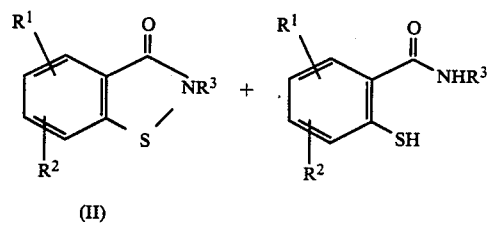

where $R^1$ to $R^3$ are for example hydrogen, halogen or low-molecular alkyl or alkoxy.

Disproportionations of this type have been described by A. Reissert and E. Manns in Chem. Ber. 61, 1308 and 1309 (1928). The reverse reaction is likewise known (German Laid-Open Application DOS No. 2,656,227).

German Laid-Open Applications DOS No. 2,652,201 and DOS No. 1,147,947 reveal that certain substituted amides of 2,2'-dithiodibenzoic acid can be converted to benzisothiazolones by treatment with aqueous alkali metal hydroxide solutions. Furthermore, according to German Laid-Open Application DOS No. 1,135,468, 6-chlorobenzisothiazolone is prepared by dissolving 4,4'-dichlorodithio-2,2'-dibenzamide in dilute sodium hydroxide solution. The resulting sodium salt of benzisothiazolone is then precipitated with sodium chloride, and the product is obtained by acidification with HCl in 65% yield.

All the methods described have the disadvantage that thiosalicylamides are formed at the same time as the desired product, thereby significantly reducing the yields to, in general, about 50% or below.

It is an object of the invention to affect the reaction in such a way as to obtain 1,2-benzisothiazolone in the highest possible yield and in high purity.

We have found that this object is achieved and that 1,2-benzisothiazolones and their alkali metal salts can advantageously be prepared by reacting 2,2'-dithiodibenzamides of the general formula (I)

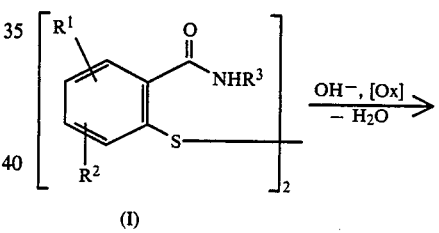

in which $R^1$ and $R^2$ are identical or different and are each hydrogen, halogen, alkyl, haloalkyl or alkoxy of 1 to 6 carbon atoms, aryl or aralkoxy and aralkyl or alkylaryl of up to 12 carbon atoms or in which $R^1$ and $R^2$ together form an aliphatic or aromatic ring and in which $R^3$ is hydrogen, alkyl of 1 to 6 carbon atoms or aryl or alkylaryl of 6 to 10 carbon atoms, in an aqueous alkaline medium thorough mixing of in the presence of oxygen donors or in the presence of oxygen while ensuring the reaction mixture with oxygen during the reaction, and if desired freeing the benzisothiazolones from the alkali metal salts with acids.

The process according to the invention unexpectedly produces the benzisothiazolones in high yield and purity. The success of this process is also surprising because it is known that benzisothiazolones are readily oxidized to the corresponding saccharins, for example by reaction with permanganate or by $H_2O_2$ oxidation in glacial acetic acid, as described by H. Hettler in Adv. Het. Chem. 15, (1973), 241

The reaction can be represented by the following diagram:

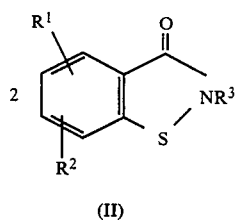

The 2,2'-dithiodibenzamide starting materials of the general formula (I) are obtainable from the corresponding acyl chlorides in a conventional manner or can be prepared, using the method described in Application No. P 34 11 385.1 by the same applicant, by reacting anthranilamides with nitrous acid and sulfur dioxide.

$R^1$ and $R^2$ shown in the formulae (I) and (II) are identical or different and are in the ortho-, meta- or para-position to the carbonyl group. They are hydrogen, halogen, in particular bromine and chlorine, alkyl of 1 to 6 carbon atoms, for example methyl, ethyl, propyl, isopropyl, butyl, isobutyl, n- and iso-butyl and n- and iso-hexyl, which may be substituted by groups which are inert under the reaction conditions, for example by cyano or nitro and in particular by fluorine, chlorine or bromine, or are each alkoxy or aralkoxy of 1 to 6, in particular 1 to 4 or 6 or 10, respectively, carbon atoms, for example methoxy, ethoxy or phenoxy.

$R^1$ and $R^2$ can each also be aryl, aralkyl or alkylaryl of 6 to 12, in particular 6 to 10, carbon atoms. Examples are phenyl, naphthyl, benzyl and phenylethyl. The aromatic nuclei may additionally carry substituents which are inert under the reaction conditions, such as halogen or alkoxy.

If $R^1$ and $R^2$ are in the ortho-position to each other, they can also from together a substituted or unsubstituted aliphatic or aromatic ring of 5 or 6 carbon atoms, for example a cyclopentyl or cyclohexyl ring.

$R^3$ is substituted or unsubstituted aryl or alkylaryl of 6 to 10 carbon atoms, preferably phenyl, which may be substituted, for example by halogen, or is substituted or unsubstituted alkyl of 1 to 6, preferably 1 to 4, carbon atoms or hydrogen.

The reaction is generally carried out be suspending the 2,2'-dithiodibenzamide (I) in from 100 to 10,000% by weight of water, based on (I), and adding an alkali metal hydroxide solution, for example potassium hydroxide or sodium hydroxide solution. The base, which is preferably in the form of a dilute, for example 50% strength, aqueous solution, is added in an amount of from 2 to 12 moles, in particular from 3 to 8 moles, per mole of starting material (I), so that the pH is from 7.5 to 14. In total the solvent is used in an amount of from 100 to 10,000 preferably from 200 to 2,000, % by weight, based on the starting material (I).

Oxygen or an oxygen donor is then added to this reaction mixture, preferably in an amount of from 1.0 to 10.0, in particular from 1.0 to 3.0, moles per mole of (I). Very suitable oxidizing agents incluse not only organic peracids, for example peracetic acid, perbenzoic acid or perphthalic acid, but also inorganic compounds such as sodium perborate, permanganate or in particular $H_2O_2$. Advantageously it is also possible to use oxygen in the reaction by ensuring that the reaction mixture is thoroughly mixed with oxygen, for example by passing an airstream through the solution. In general, an excess of oxygen is used.

Instead of carrying out the reaction in a purely aqueous medium, which constitutes the preferred embodiment when the reaction is carried out in the presence of readily water-soluble compounds, it is also possible to use an aqueous organic solvent mixture. It is advantageous to add water-soluble organic solvents such as alcohols, for example ethanol or isopropanol, or glycols, for example ethylene glycol.

The reaction temperature is in general from 30° to 80° C., preferably from 50° to 70° C. It can also be advantageous to use two temperature ranges by starting the reaction at a low temperature of about 30°–40° C. and completing the reaction at elevated temperatures of from about 50° to 70° C.

The reaction is generally complete after 3–4 hours. In the case of unsubstituted amides of 2,2'-dithiodibenzoic acids being used as starting material, the alkali metal salts of the 1,2-benzisothiazolones are obtained directly as precipitate on cooling down the aqueous solution without any need for salting out. The process can also be operated continuously if it is desired to obtain the alkali metal salts which are readily soluble in aqueous organic solvent mixtures and find utility as biocides.

If the free 1,2-benzisothiazolones are to be obtained, the reaction mixture if acidified, for example with dilute hydrochloric acid, and the precipitated solid is isolated in a conventional manner, for example by filtration.

The compounds prepared using the process according to the invention have biological activity and are used inter alia as bactericides (British Pat. No. 861,379), fungicides (U.S. Pat. No. 3,761,489) and pharmaceuticals (European Pat. Nos. 51,193 and 101,786).

EXAMPLE 1

40.4 g of 2,2'-dithiodibenzamide were suspended in 136.0 g of $H_2O$. 32.0 g of NaOH were added as a 50% strength solution, and the mixture was heated to 35° C. An airstream of 60 l/h was passed with stirring through the solution for 3.5 hours. Losses of water were replaced continuously. The temperature was raised to 55° C. one hour after the start of the reaction. After 3.5 hours the batch was cooled to 20° C. and was acidified with 40.0 g of 30% strength HCl. The precipitate was filtered off with suction and dried, giving 37.1 g of pure 1,2-benzisothiazolone having a melting point of from 155° to 156° C. and a purity of 97%. The yield was 94% of theory.

EXAMPLE 2

37.3 g of 4,4'-dichloro-2,2'-dithiodibenzamide were dissolved with 19.6 g of KOH in 250 ml of $H_2O$. The temperature was raised to 60° C. 38 g of a 10% strength solution of $H_2O_2$ in $H_2O$ were added dropwise to the reaction flask in the course of two hours. Stirring was continued at 50° C. for one hour, and the batch was then cooled down to 20° C. After acidification with 60 g of 30% strength HCl the precipitate was filtered off with Suction and washed with a little water. Drying left 36.4 g of 6-chlorobenzisothiazolone having a melting point of from 273° to 274° C.

We claim:

1. In a process for preparing 1,2-benzisothiazolones and their alkali metal salts by reacting 2,2'-dithiodibenzamides in an aqueous alkaline solution, the improvement which comprises reacting 2,2'-dithiodibenzamides of the formula

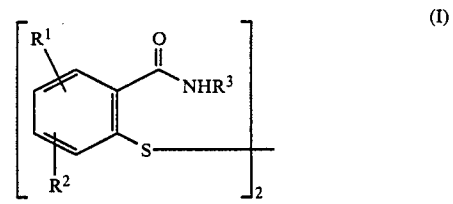

in which $R^1$ and $R^2$ are identical or different and are each hydrogen, halogen, alkyl, haloalkyl or alkoxy of 1 to 6 carbon atoms, aryl or aralkoxy and aralkyl or alkylaryl of up to 12 carbon atoms, or in which $R^1$ and $R^2$ together form an aliphatic or aromatic ring and in which $R^3$ is hydrogen, alkyl of 1 to 6 carbon atoms or aryl or alkylaryl of 6 to 10 carbon atoms, in the presence of oxygen supplied to the reaction mixture in an amount of 1.0 to 10.0 moles per mole of the compound I while ensuring thorough mixing of the reaction mixture with oxygen during the reaction.

2. A process as claimed in claim 1, wherein the reaction is carried out with an excess of oxygen.

3. A process as claimed in claim 1, wherein the reaction is carried out in the presence of excess atmospheric oxygen by passing an airstream through the solution.

4. A process as claimed in claim 1, wherein the oxygen is supplied by an oxygen donor selected from the group consisting of hydrogen peroxide, sodium perborate, potassium permanganate and organic per-acids.

5. A process as claimed in claim 4, wherein the oxygen donors are used in an amount of from 1.0 to 10 moles per mole of 2,2'-dithiodibenzamide.

6. A process as claimed in claim 1, wherein the reaction is carried out at from 30° to 80° C.

7. A process as claimed in claim 1, wherein the aqueous solvent is used in an amount of from 100 to 10,000% by weight, based on the 2,2'-dithiodibenzamide.

8. A process as claimed in claim 1, wherein from 2 to 12 moles of alkali metal hydroxide in aqueous solution are used per mole of 2,2'-dithiodibenzamide.

9. A process as claimed in claim 1, wherein a water-soluble organic solvent is added to the aqueous alkaline medium.

10. A process as claimed in claim 9 wherein the added organic solvent is selected from the group consisting of readily water-soluble alcohols and glycols.

11. A process as claimed in claim 10 wherein the added organic solvent is selected from the group consisting of ethanol, isopropanol and ethylene glycol.

12. A process as claimed in claim 1 wherein the free 1,2-benzisothiazolone is obtained after the reaction is completed by acidifying the reaction mixture.

13. A process as claimed in claim 12 wherein the reaction mixture is acidified with dilute hydrochloric acid.

14. A process as claimed in claim 12 wherein the freed 1,2-benzisothiazolone is precipitated and isolated from the reaction mixture.

* * * * *